(12) United States Patent
Kim et al.

(10) Patent No.: US 11,168,108 B2
(45) Date of Patent: Nov. 9, 2021

(54) COMPOSITION FOR ADJUSTING BIOLOGICAL TISSUE SIZE, AND METHOD FOR ADJUSTING SIZE OF BIOLOGICAL TISSUE USING SAID COMPOSITION

(71) Applicant: KOREA RESEARCH INSTITUTE OF CHEMICAL TECHNOLOGY, Daejeon (KR)

(72) Inventors: Ki-Suk Kim, Daejeon (KR); Sun Hyun Park, Daejeon (KR); Dae-hwan Nam, Daegu (KR)

(73) Assignee: KOREA RESEARCH INSTITUTE OF CHEMICAL TECHNOLOGY

( * ) Notice: Subject to any disclaimer, the term of this patent is extended or adjusted under 35 U.S.C. 154(b) by 0 days.

(21) Appl. No.: 16/473,365

(22) PCT Filed: Aug. 3, 2018

(86) PCT No.: PCT/KR2018/008842
§ 371 (c)(1),
(2) Date: Jun. 25, 2019

(87) PCT Pub. No.: WO2019/039767
PCT Pub. Date: Feb. 28, 2019

(65) Prior Publication Data
US 2020/0140479 A1    May 7, 2020

(30) Foreign Application Priority Data

Aug. 24, 2017   (KR) ........................ 10-2017-0107294

(51) Int. Cl.
*C07J 41/00*      (2006.01)
*A61L 27/36*      (2006.01)
*G01N 33/483*     (2006.01)

(52) U.S. Cl.
CPC ....... *C07J 41/0038* (2013.01); *A61L 27/3687* (2013.01); *G01N 33/4833* (2013.01)

(58) Field of Classification Search
CPC ............... C07J 41/0038; C07J 41/0061; A61L 27/3687; G01N 1/30; G01N 33/4833
See application file for complete search history.

(56) References Cited

U.S. PATENT DOCUMENTS

| | | | | |
|---|---|---|---|---|
| 5,413,938 A | * | 5/1995 | Tsujino | G01N 33/5094 436/63 |
| 2013/0045503 A1 | * | 2/2013 | Miyawaki | G01N 1/30 435/40.5 |
| 2016/0377514 A1 | | 12/2016 | Simon et al. | |

FOREIGN PATENT DOCUMENTS

| | | |
|---|---|---|
| JP | H06-273413 | 9/1994 |
| JP | 2003-329668 | 11/2003 |
| JP | 2004-101345 | 4/2004 |
| JP | 4025153 | 12/2007 |
| JP | 4212827 | 1/2009 |
| JP | 2013-522590 | 6/2013 |
| JP | 2015-049101 | 3/2015 |
| JP | 2017108684 | 6/2017 |
| KR | 10-1994-0022088 | 10/1994 |
| KR | 10-0287583 | 5/2001 |
| KR | 10-2017-0051443 | 5/2017 |
| KR | 10-2017-0079449 | 7/2017 |
| KR | 10-1849698 | 4/2018 |
| WO | WO 2009/001869 | 12/2008 |
| WO | WO2016023009 | * 2/2016 |

OTHER PUBLICATIONS

International Search Report for International (PCT) Patent Application No. PCT/KR2018/008842, dated Feb. 18, 2019, 2 pages.

\* cited by examiner

*Primary Examiner* — Barbara P Badio
(74) *Attorney, Agent, or Firm* — Sheridan Ross P.C.

(57) ABSTRACT

The present invention provides a composition for adjusting biological tissue size and a method for adjusting the size of biological tissue using the said composition. The composition for adjusting the size of biological tissue according to the present invention can adjust the size of biological tissue according to the specifications of a microscope and the needs of a researcher, and can be used as a mounting solution to easily acquire an image of the biological tissue. Therefore, the composition can be usefully used to reveal the causes of and find treatment methods for various disorders.

12 Claims, 8 Drawing Sheets

(8 of 8 Drawing Sheet(s) Filed in Color)

COMPOSITION FOR ADJUSTING BIOLOGICAL TISSUE SIZE, AND METHOD FOR ADJUSTING SIZE OF BIOLOGICAL TISSUE USING SAID COMPOSITION

CROSS REFERENCE TO RELATED APPLICATIONS

This application is a national stage application under 35 U.S.C. 371 and claims the benefit of PCT Application No. PCT/KR2018/008842 having an international filing date of 3 Aug. 2018, which designated the United States, which PCT application claimed the benefit of the Republic of Korea Patent Application No. 10-2017-0107294 filed 24 Aug. 2017, the disclosure of each of which are incorporated herein by reference.

BACKGROUND OF THE INVENTION

1. Field of the Invention

The present invention relates to a composition for adjusting biological tissue size and a method for adjusting the size of biological tissue using the said composition.

2. Description of the Related Art

The medical diagnostic techniques using x-ray have been developed as a technology capable of diagnosing a disease precisely from three-dimensional observation of images obtained from two-dimensional scanning such as CT or MRI. When ultrasound is used instead of a light source, a technique for realizing a three-dimensional image has also been widely used for diagnosis. However, most of the techniques developed so far have a millimeter level resolving power which materializes image in millimeters. The technology of measuring the micro level that can be analyzed at the cell level in three dimensions is relatively inadequate. Most cases of cell level analysis are performed by traditional two-dimensional techniques. That is, a biological tissue sample such as a biopsy tissue or an autopsy tissue is fixed with a fixative, embedded in paraffin or polymer, and then sections are prepared therefrom in micrometer or nanometer thickness so that light or electromagnetic wave can pass through. Then, the microstructure is analyzed using a technique of acquiring transmission images using an optical or electron microscope.

In order to obtain a three-dimensional image of a sample using such a fine imaging technique, a confocal microscope has to be used. In this case, information in thickness of tens of micrometers can be obtained. In general, the thickness is limited by the depth at which the light source can penetrate. However, significant structures in most living tissues have the size of several hundred micrometers or more, and thus only a part of information can be acquired by such a method.

Therefore, in order to obtain a thicker tissue image, a series of pieces of continuous sections of several tens of micro-thicknesses are prepared, and then a series of processes are carried out by imaging the images through a microscope and reconstructing them again. Therefore, in order to obtain an image in the inside of a thicker tissue, a series of pieces of continuous sections in the thickness of tens of micrometers have to be prepared first and imaging of each section has to be performed by using a microscope and then re-construction process is needed. In particular, when imaging a whole neuron in the brain tissue, a series of steps of cutting, adhering and re-forming the tissue are required because one neuron might stretch its axon out up to a few meters, during which there is a risk of many unwanted problems.

On the other hand, a tissue clearing technique facilitates the investigation of the inside structure and protein distribution in tissue without damaging the tissue, which overcomes the limit of the conventional technique and makes it possible to observe a deeper tissue structure and to approach the integral structure and molecular information of various systems. Therefore, tissue clearing techniques have been developed via various approaches. Along with the advancement of such a tissue clearing technology, various mounting solutions have also been developed to observe the vitrified tissue more clearly under a microscope. However, there is no report about a mounting solution that can adjust the size of tissue, particularly the vitrified giant tissue. In addition, the price of mounting solutions currently in commercial use is too high. For example, in the case of focus clearing solution, the consumer price is 500,000 Korean Won including tax per 5 mL.

The present inventors have developed a composition for clearing biological tissue and a method for clearing biological tissue using the same. Particularly, the present inventors filed a patent application for a composition for clearing biological tissue characterized by not requiring an expensive electrophoresis apparatus and an expensive solution, being applied to various biological tissues such as brain, liver, lung, kidney, intestine, heart, muscle, and blood vessel without damaging them, improving transparency of the biological tissue without bubble formation, discoloration and black deposit, and allowing antibody staining in the vitrified tissue (application No. 10-2017-0051443).

Subsequently, the present inventors developed a mounting solution that can regulate the size of the vitrified biological tissue according to the specifications of a microscope and the needs of a researcher without causing any other changes in the tissue such as protein damage and tissue denaturation, leading to the completion of the present invention.

In relation to the above, US Patent Publication No. 2016/0377514 describes a mounting solution comprising trichloroethanol.

SUMMARY OF THE INVENTION

It is an object of the present invention to provide a composition for adjusting biological tissue size and a method for adjusting the size of biological tissue using the composition above.

To achieve the object above, the present invention provides a composition for adjusting biological tissue size comprising a compound represented by formula 1 below, an optical isomer thereof, a hydrate thereof, or a salt thereof and an alkali metal halide.

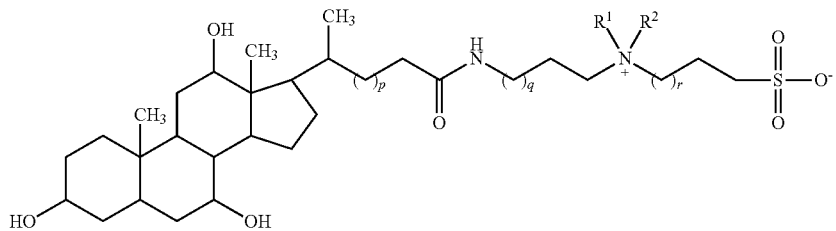

[Formula 1]

In formula 1 above,

R¹ and R² are independently $C_{1-10}$ straight or branched alkyl; and p, q and r are independently an integer of 0~10.

The present invention also provides a method for adjusting the size of biological tissue which includes a step of adjusting the size of the tissue by contacting the biological tissue with the said composition.

Advantageous Effect

The composition for adjusting the size of biological tissue according to the present invention can adjust the size of biological tissue according to the specifications of a microscope and the needs of a researcher, and can be used as a mounting solution to easily acquire an image of the biological tissue. Therefore, the composition can be usefully used to reveal the causes of and find treatment methods for various disorders.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

DESCRIPTION OF THE PREFERRED EMBODIMENTS

Figure 1A:
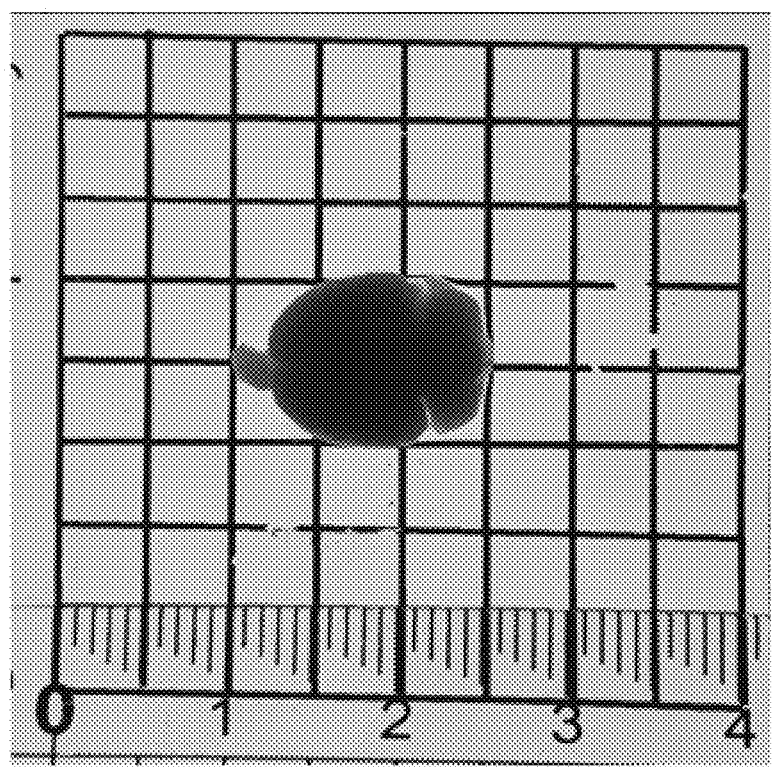
FIGS. 1 to 5 are photographs illustrating the biological tissues obtained from each step performed to prepare a vitrified biological tissue according to an example of the present invention.

The present invention provides a composition for adjusting biological tissue size comprising a compound represented by formula 1 below, an optical isomer thereof, a hydrate thereof, or a salt thereof and an alkali metal halide.

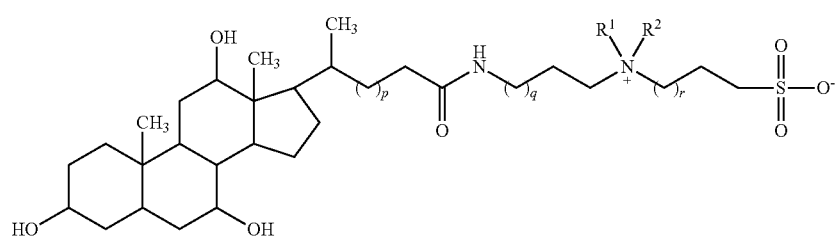

[Formula 1]

In formula 1 above,
R¹ and R² are independently $C_{1-10}$ straight or branched alkyl; and p, q and r are independently an integer of 0~10.
Preferably,
R¹ and R² are independently $C_{1-5}$ straight or branched alkyl; and p, q and r are independently an integer of 0~5.
More preferably,
R¹ and R² are methyl; and
p, q and r are an integer of 1.
Most preferably, the compound represented by formula 1 is a compound represented by the following formula 2 or a hydrate thereof.

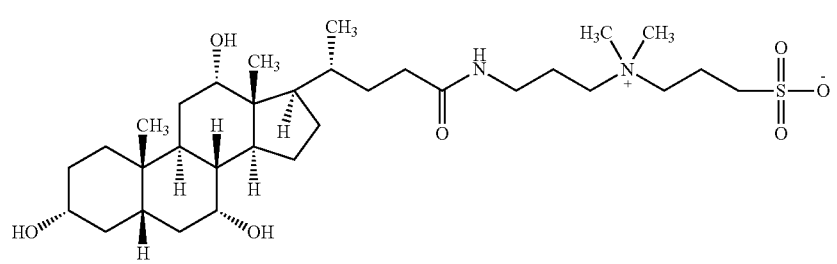

[Formula 2]

Hereinafter, the composition for adjusting biological tissue size according to the present invention is described in detail.

The composition for adjusting biological tissue size according to the present invention can adjust the size of biological tissue by controlling the content and the concentration of each constituent.

In the present invention, the composition for adjusting biological tissue size is prepared for easy observation of a biological tissue under a microscope, in which the biological tissue can be a vitrified biological tissue.

The composition for clearing biological tissue used for obtaining a vitrified biological tissue can be a composition that is commonly used, and preferably the composition for clearing biological tissue can include the compound represented by formula 1. At this time, the concentration of the compound is 2~55 w/v % (weight/volume %) and preferably 20~50 w/v %. The solution for the concentration can be a simulated body fluid which has been generally used in this field. More specifically, distilled water, PBS (phosphate buffer saline or TBS (tris buffer solution) can be used, but not always limited thereto.

If the concentration of the compound represented by formula 1 above is less than 2 w/v %, the rate of clearing the biological tissue would be slowed. On the other hand, if the concentration of the compound is more than 55 w/v %, the CHAPS represented by formula 1 above would not be dissolved completely.

Further, the composition for clearing biological tissue can additionally include a substance that can accelerate the progress of biological tissue clearing by controlling osmotic pressure. At this time, the substance that can accelerate the progress of biological tissue clearing is exemplified by urea, CHAPSO (3-([3-Cholamidopropyl]dimethylammonio)-2-hydroxy-1-propanesulfonate), sucrose, fructose, glycerol, diatrizoic acid, Triton X-100, Tween-20, 2,2'-thiodiethanol, iohexol, chloral hydrate, or a combination thereof, but not always limited thereto.

At this time, the substance accelerating biological tissue clearing can be included at the concentration of 5~80 w/v %, preferably 5~75 w/v %, more preferably 10~70 w/v %, 5~50 w/v %, and most preferably 35~60 w/v. At this time, if the concentration of the substance is less than 5 w/v %, the rate of tissue clearing would be slowed. On the other hand, if the concentration of the substance is more than 80 w/v %, crystals would be formed or not dissolved in the solution. As an example, in the case of using urea as the substance accelerating biological tissue clearing, the concentration of urea can be 10~70 w/v % and more preferably 20~60 w/v %. In addition, the concentration of the substance accelerating biological tissue clearing can be appropriately adjusted to the preferable concentration range of the compound represented by formula 1 above.

Once the biological tissue is vitrified by the composition for clearing biological tissue, the size of the biological tissue can be adjusted by using the composition for adjusting biological tissue size of the present invention.

The composition for adjusting biological tissue size according to the present invention can include a compound represented by formula 1, an optical isomer thereof, a hydrate thereof, or a salt thereof and an alkali metal halide.

At this time, the said composition can additionally include urea, CHAPSO (3-([3-Cholamidopropyl]dimethylammonio)-2-hydroxy-1-propanesulfonate), sucrose, fructose, glycerol, diatrizoic acid, Triton X-100, Tween-20, 2,2'-thiodiethanol, iohexol, chloral hydrate, or a combination thereof, and more preferably include urea.

The composition for adjusting biological tissue size can additionally include a simulated body fluid. In the mixture of the composition for adjusting biological tissue size and the simulated body fluid, the concentration of the compound represented by formula 1 above, the optical isomer thereof, the hydrate thereof or the salt thereof can be 30~60 w/v % and the concentration of the alkali metal halide can be 1~5 w/v %.

The alkali metal halide can comprise any form of alkali metal and halogen element combined, which is preferably sodium chloride.

As described hereinbefore, the composition for adjusting biological tissue size according to the present invention can adjust the size of the vitrified biological tissue without damaging the tissue; can be applied to various biological tissues such as brain, liver, lung, kidney, intestine, heart, muscle, and blood vessel without damaging them; can prevent tissues from swelling, bubble formation, discoloration and black deposit; and is not expensive, so that it can be effectively used as a composition for adjusting biological tissue size.

The present invention also provides a method for adjusting the size of biological tissue which includes a step of adjusting the size of the tissue by contacting the biological tissue with the said composition for adjusting biological tissue size.

Hereinafter, the method for adjusting biological tissue size according to the present invention is described in more detail.

The biological tissue according to the present invention can be a vitrified tissue, and the method for adjusting the size of the vitrified tissue includes a step of adjusting the size of the tissue by contacting the vitrified tissue with the composition above.

Particularly, the method for adjusting the size of the vitrified tissue according to the present invention is accomplished by contacting the vitrified tissue with the composition comprising the compound represented by formula 1 to adjust the size by inducing changes in physiochemical characteristics of the biological tissue, by which images thereof can be easily obtained through a microscope.

In this invention, fixation of the biological tissue is necessary in order to prepare the vitrified biological tissue. The method for fixing biological tissue can be used without any particular limitation.

More particularly, the method for fixing biological tissue can be performed by the conventional method using paraformaldehyde, ethylene glycol diglycidyl ether, dipropylene glycol diglycidyl ether, 1,4-butanediol diglycidyl ether, glycerol polyglycidyl ether, glutaraldehyde, polyacrylamide or a combination thereof, but not always limited thereto.

In a preferred embodiment of the present invention, the tissue size can be adjusted by treating the tissue with the composition for adjusting biological tissue size which is the mixture of CHAPS, urea and an alkali metal halide.

A solution for regulating the concentration above can be a simulated body fluid generally used in this field, or can be distilled water, PBS (phosphate buffer saline) or TBS (tris buffer solution), but not always limited thereto. Soaking can be performed at the temperature range of 10° C. to 50° C., preferably at the temperature range of 12° C. to 48° C., at the temperature range of 14° C. to 46° C., at the temperature range of 16° C. to 44° C., at the temperature range of 18° C. to 42° C., at the temperature range of 20° C. to 40° C., at the temperature range of 24° C. to 39° C., at the temperature range of 28° C. to 38° C., at the temperature range of 30° C. to 37° C., and at the temperature range of 33° C. to 34° C.

In the case that the composition for adjusting biological tissue size includes a simulated body fluid additionally, the concentration of CHAPS in the mixed solution comprising the composition for adjusting biological tissue size and the simulated body fluid can be 30 w/v %~60 w/v % and the concentration of the alkali metal halide can be 1 w/v %~5 w/v %.

At this time, the alkali metal halide can comprise any form of alkali metal and halogen element combined, which is preferably sodium chloride.

The method for adjusting biological tissue size according to the present invention can be applied to various vertebrate tissues, particularly to brain, blood vessel, liver, lung, kidney, pancreas, intestine, heart, etc, and the composition can adjust the size of the entire tissue at once.

The method of the present invention facilitates the regulation of the size of the vitrified tissue without damaging the tissue and thereby imaging the three dimensional distribution of cells and molecules for better observation. Therefore, the method of the present invention is advantageous for the observation and study of various biological tissues having a complicated structure as a whole structure in the size of hundreds of micrometers and also for obtaining useful information from the tissue to be useful for finding causes of various diseases including brain disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXPERIMENTAL EXAMPLE 1: CHANGES OF VITRIFIED BIOLOGICAL TISSUE SIZE

The following experiment was performed to investigate whether the composition according to the present invention was able to change the size of the vitrified tissue. All the animal test processes in this specification were performed in accordance with the guideline (Approval No. RS17003) of the Institutional Animal Care and Use Committee, Korea Institute of Toxicology.

1. Preparation of Vitrified Biological Tissue (Step 1)

First, adult mice (at 8 weeks) were anesthetized with isoflurane (1 cc/min), an inhalation anesthetic, followed by perfusion with 50 mL of cold 1× PBS and cold 4% PFA (paraformaldehyde) stepwise. Then, organs were extracted and immersed in 4% PFA solution, followed by incubation at 4° C. for 24 hours. At this time, the temperature above was not limited to a specific range but preferably 0~10° C.

Figure 1B:
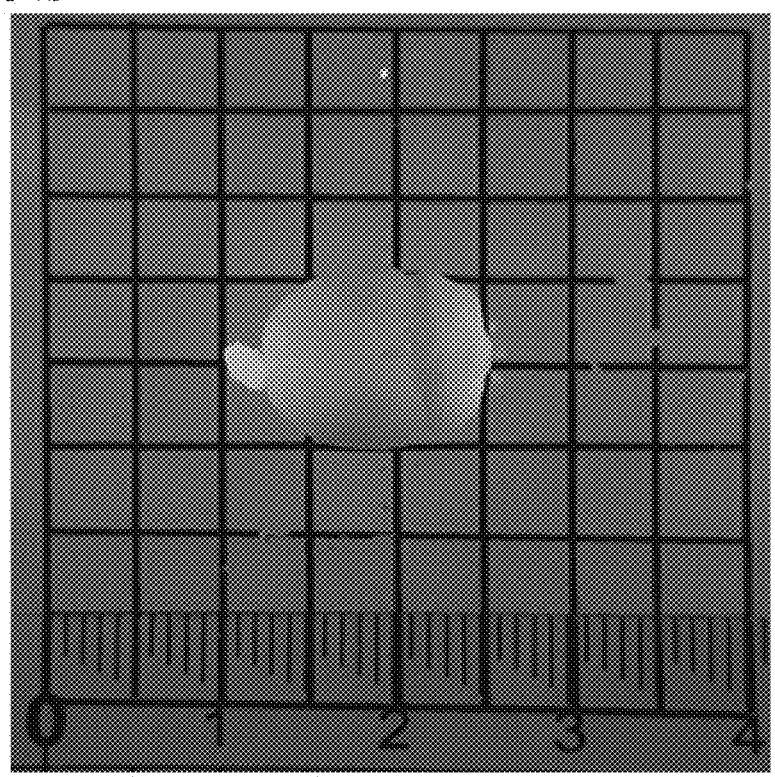

Next, the samples were incubated in the presence of 30% sucrose at 0~10° C. for 24 hours. The overall brain size was 1 cm×1.3 cm (width×length) except the part of olfactory bulb. The results are shown in FIGS. 1(a) and 1(b).

Figure 2A:
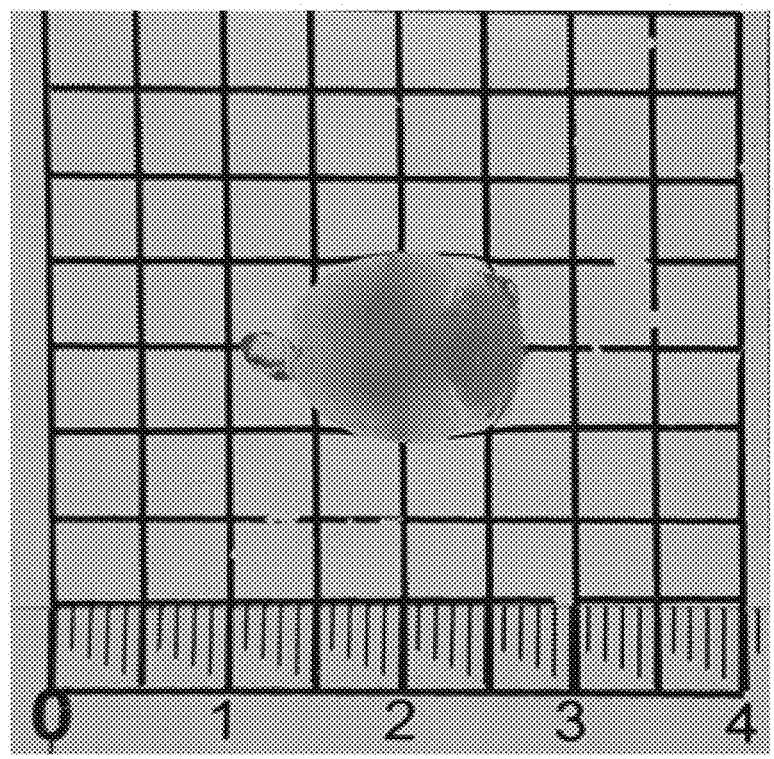
Figure 2B:
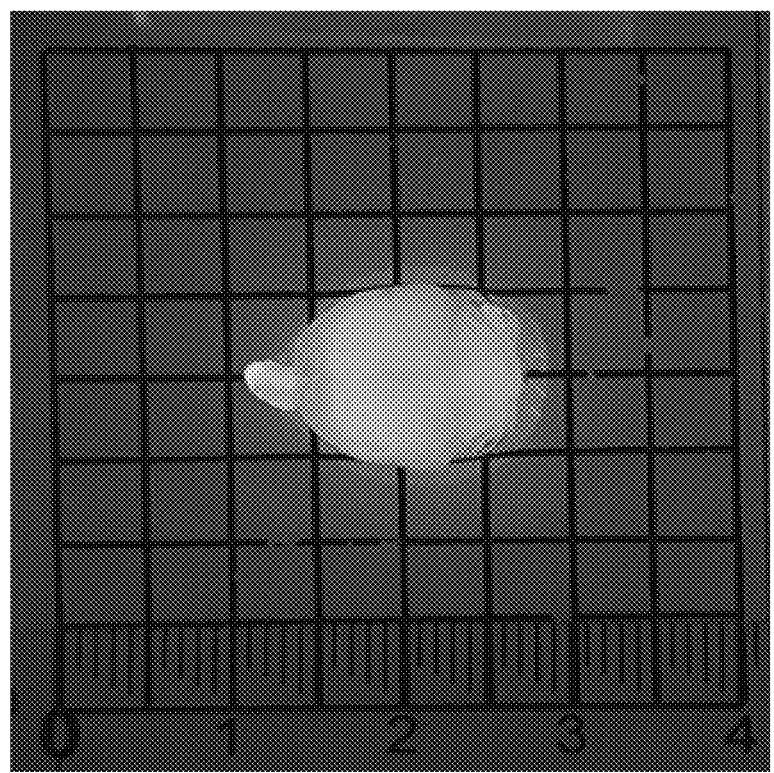

To clarify the tissue sample, shaking incubation was performed with a mixed solution comprising 25 w/v % of CHAPS, 50 w/v % of urea and 50 mM sodium azide at 35° C. at 150 rpm for 24 hours. The incubation time can be extended or shortened if necessary. The overall brain size was 1.2 cm×1.3 cm (width×length) except the part of olfactory bulb. The results are shown in FIGS. 2(a) and 2(b).

Figure 3A:
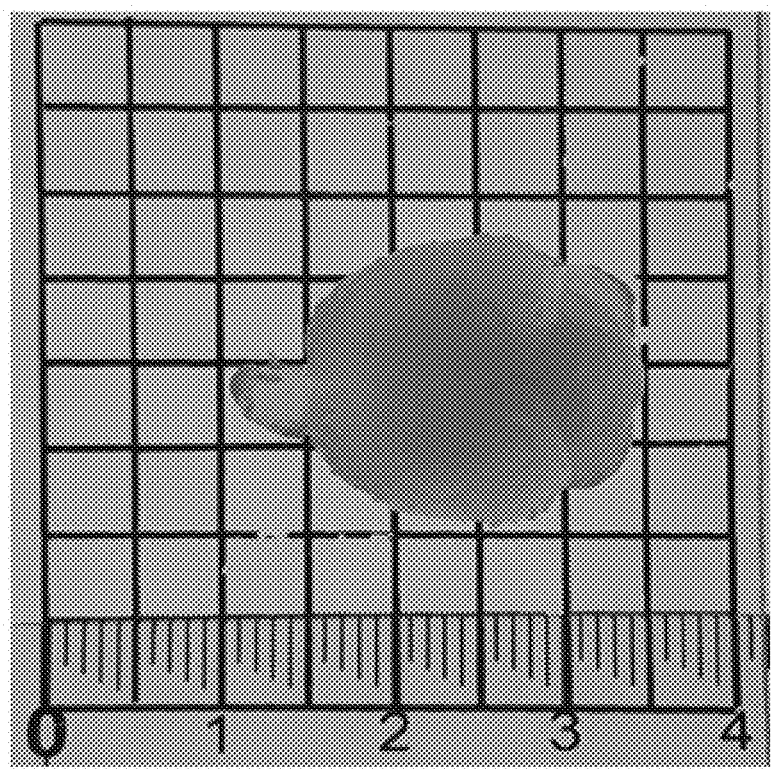
Figure 3B:
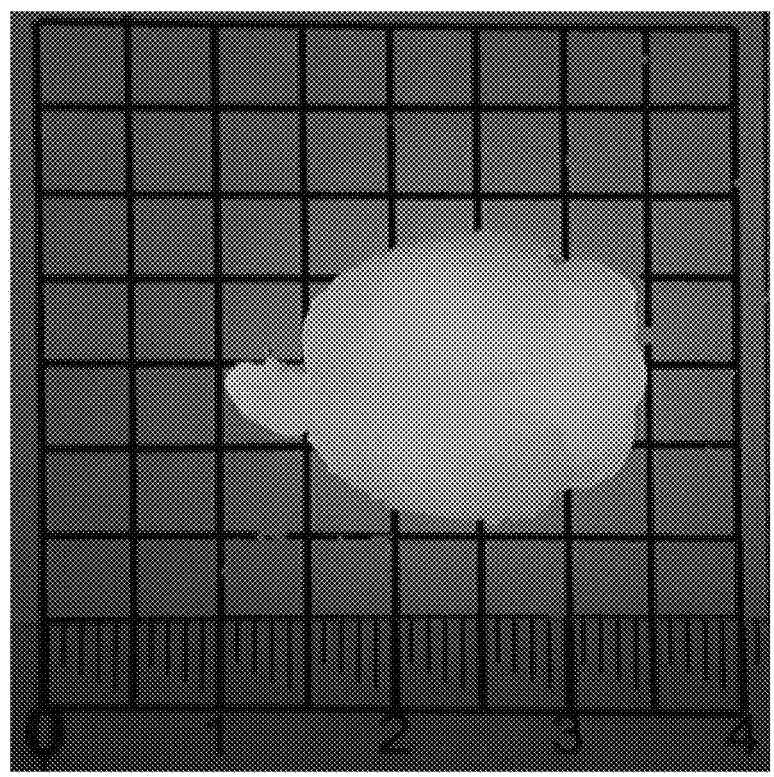

Then, incubation was performed three times with 50 mL of sterile distilled water containing PBS (phosphate buffer saline, 0.01%) at 0~10° C. at 150 rpm for 24 hours. The overall brain size was 1.3 cm×2 cm (width×length) except the part of olfactory bulb. The results are shown in FIGS. 3(a) and 3(b).

Figure 4A:
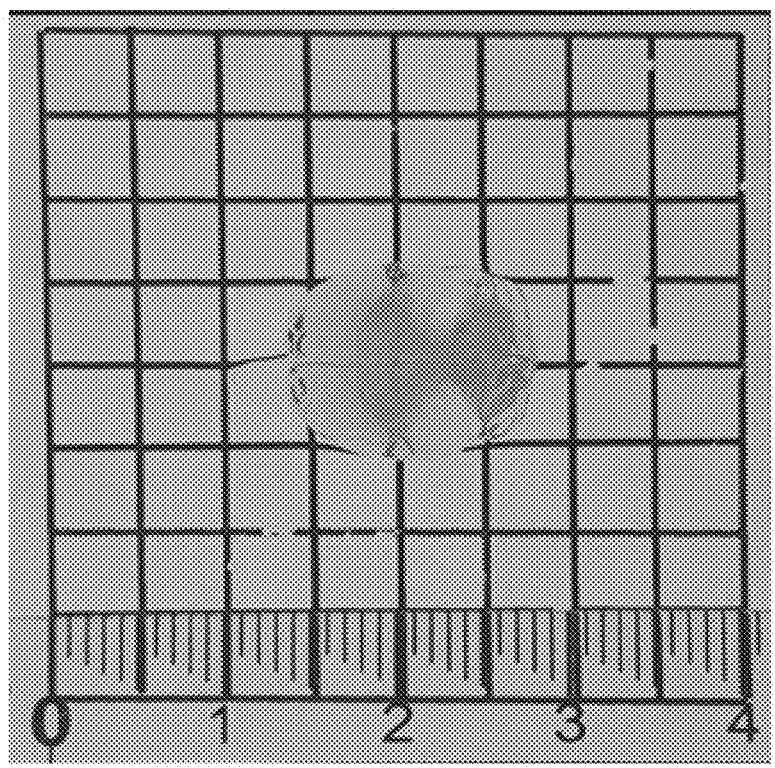
Figure 4B:
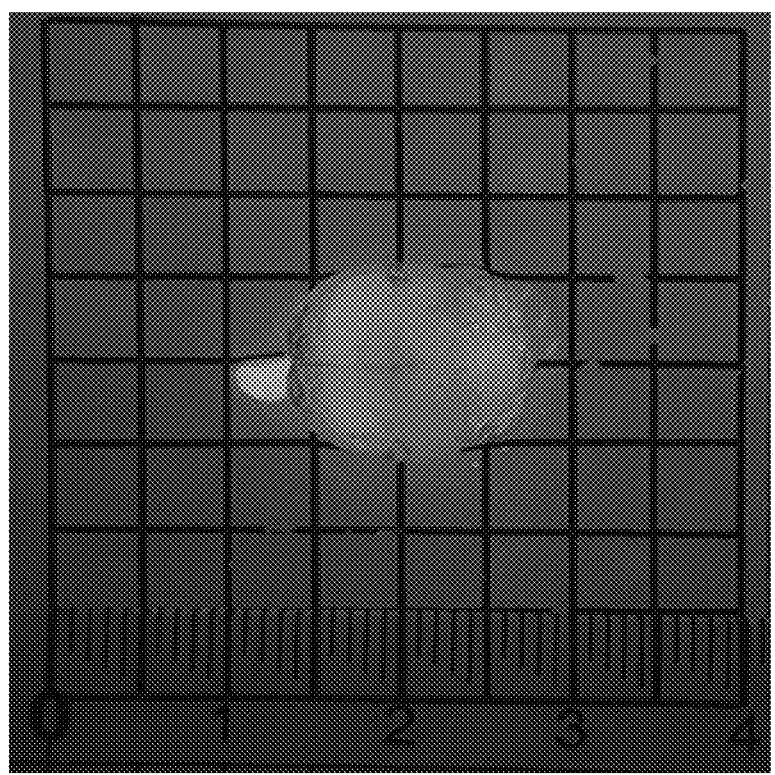

Incubation was performed again with a mixed solution comprising 20 w/v % of CHAPS, 50 w/v % of urea and 50 mM sodium azide at 35° C. at 150 rpm for 24 hours. The incubation time can be extended or shortened if necessary. The overall brain size was 1.2 cm×1.3 cm (width×length) except the part of olfactory bulb. The results are shown in FIGS. 4(a) and 4(b).

Figure 5A:
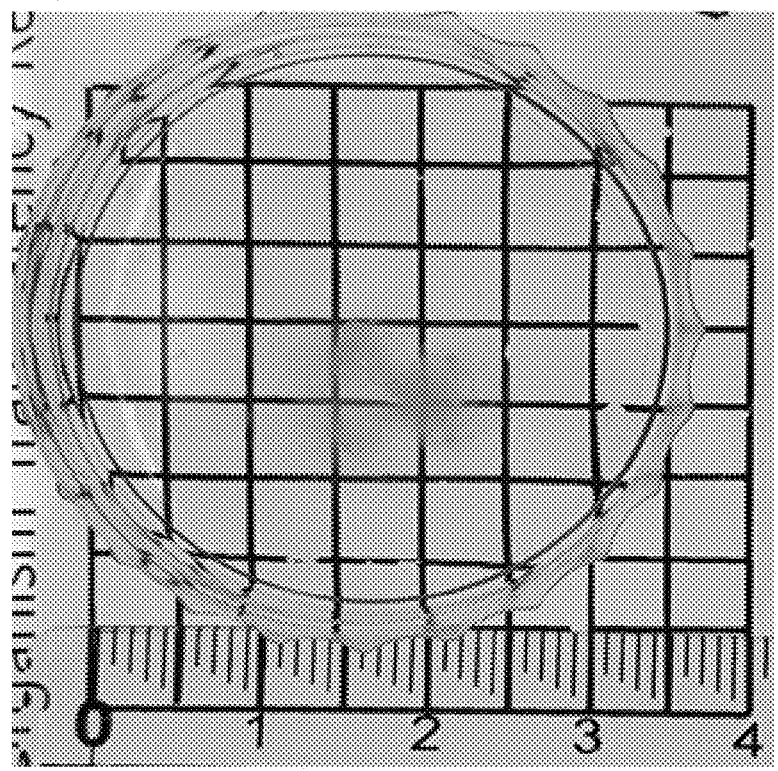
Figure 5B:
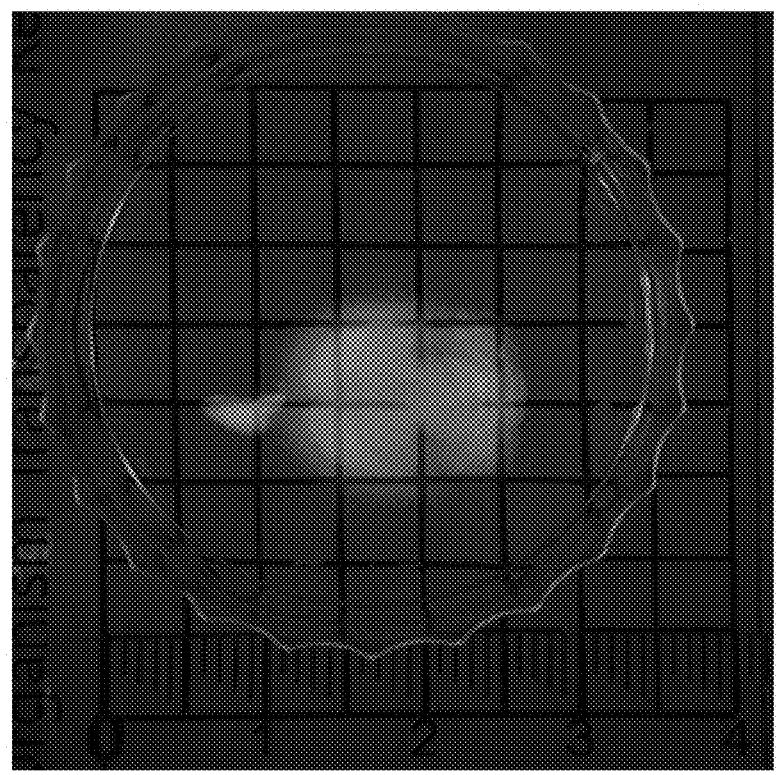

Then, incubation was also performed with a mixed solution comprising 40 w/v % of CHAPS and 40 w/v % of urea at 37° C. at 220 rpm for 24 hours. The incubation time can be extended or shortened if necessary. The overall brain size was 1.2 cm×1.3 cm (width×length) except the part of olfactory bulb. The results are shown in FIGS. 5(a) and 5(b).

The sample was vitrified through the above procedure with raising the concentration of CHAPS slowly.

2. Reduction of the Size of the Sample Prepared in Step 1 (step 2)

Figure 6A:
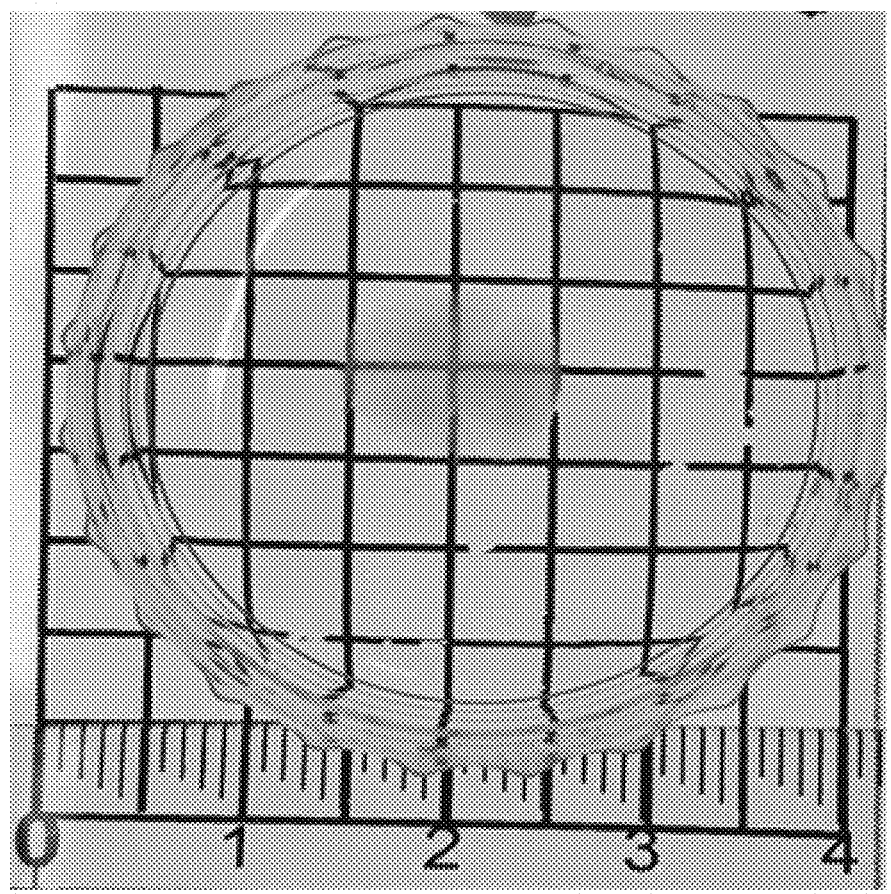
FIG. 6(a) and FIG. 6(b) are photographs illustrating the biological tissues vitrified according to an example of the present invention whose sizes had been reduced by using a mounting solution.
Figure 6B:
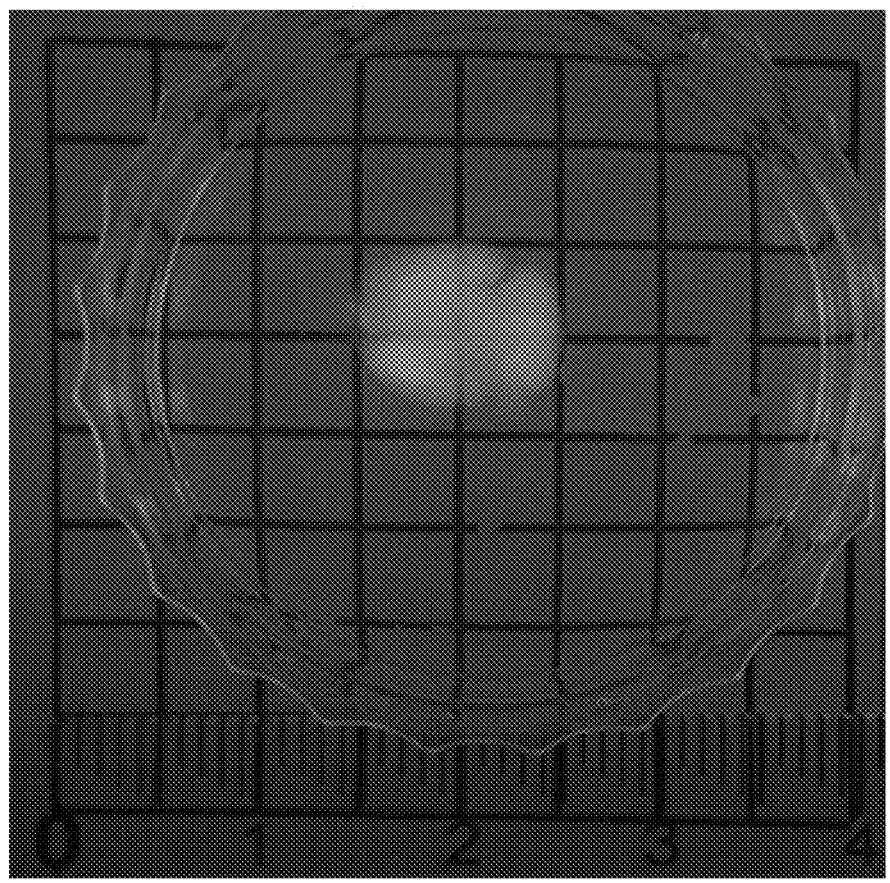

The vitrified sample prepared in step 1 was incubated in a mixed solution comprising 40 w/v % of CHAPS, 40 w/v % of urea and 50 mM sodium chloride at 35° C. at 220 rpm for 24 hours. The overall brain size was 0.8 cm×1 cm (width×length) except the part of olfactory bulb. The results are shown in FIGS. 6(a) and 6(b).

As a result, it was confirmed that the size of the vitrified tissue was reduced by the treatment of the composition of the present invention.

EXPERIMENTAL EXAMPLE 2: OBTAINING MICROSCOPE IMAGES OF THE VITRIFIED TISSUE REDUCED IN SIZE

Figure 6C:
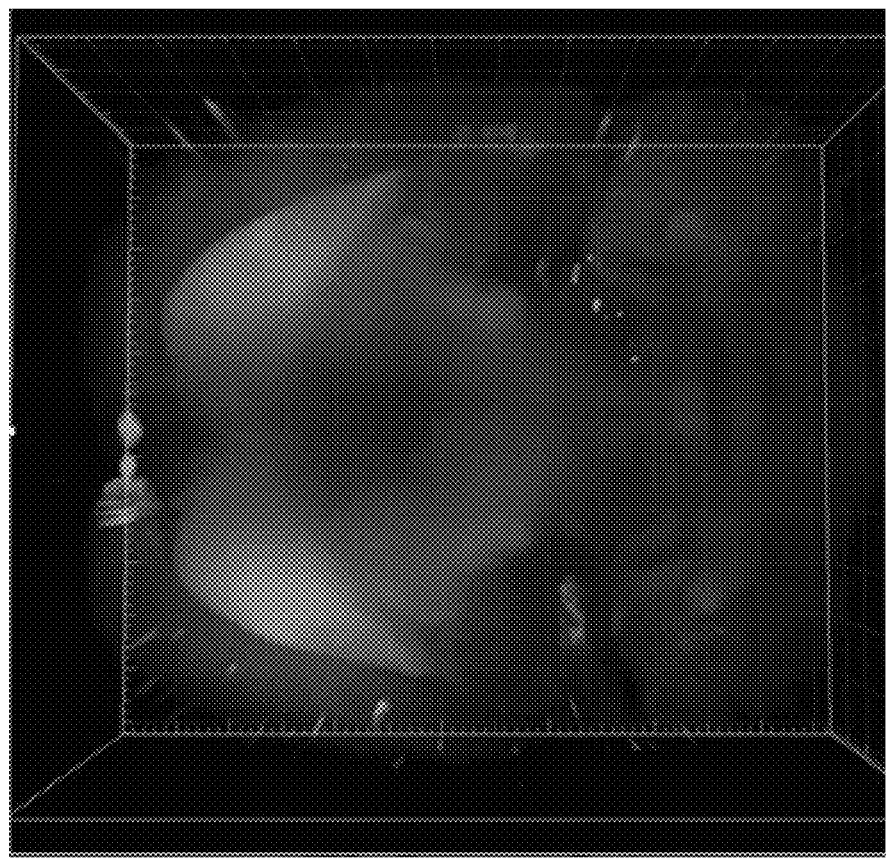
FIG. 6(c) is an image of the size-reduced biological tissue obtained through a microscope.

The size of the vitrified tissue was reduced by using the composition of the present invention, so that the sample was changed in size suitable for the observation under microscope. The vitrified brain tissue reduced in size was observed under microscope using 1X objective lens, from which green fluorescent protein (GFP) of the mouse brain was confirmed (FIG. 6(c)).

As a result, it was confirmed that the desired image can be easily obtained by reducing the size of the vitrified tissue to fit the microscope size.

INDUSTRIAL APPLICABILITY

The composition for adjusting biological tissue size according to the present invention can be used as a mounting solution so that it can be effectively used to obtain biological tissue images, to reveal the causes of and find treatment methods for various disorders.

What is claimed is:

1. A method for adjusting the size of biological tissue comprising a step of adjusting the size of a cleared biological tissue before microscopic observation by contacting the cleared biological tissue with a mounting solution composition comprising a compound represented by formula 2, an optical isomer thereof, a hydrate thereof, or a salt thereof, and alkali metal salt, wherein the cleared biological tissue is a biological tissue treated with a clearing composition for tissue clearing:

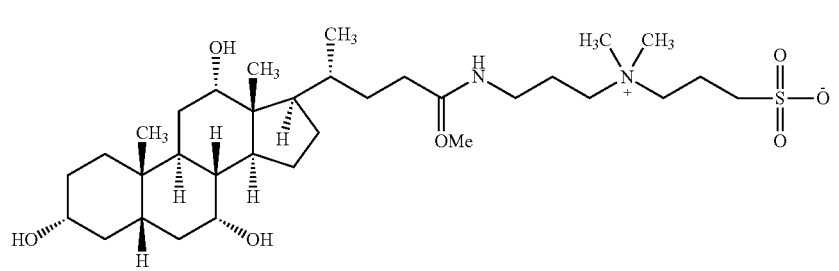
[Formula 2]

2. The method according to claim 1, wherein said contacting is performed at the temperature range of 10° C. to 50° C.

3. The method according to claim 1, wherein the mounting solution composition further comprises a simulated body fluid.

4. The method according to claim 1, wherein the step of adjusting is carried out before imaging of the biological tissue using microscope.

5. The method according to claim 1, wherein the step of adjusting is carried out after clearing the biological tissue.

6. The method according to claim 1, wherein the clearing composition comprises a compound represented by formula 2, an optical isomer thereof, a hydrate thereof, or a salt thereof:

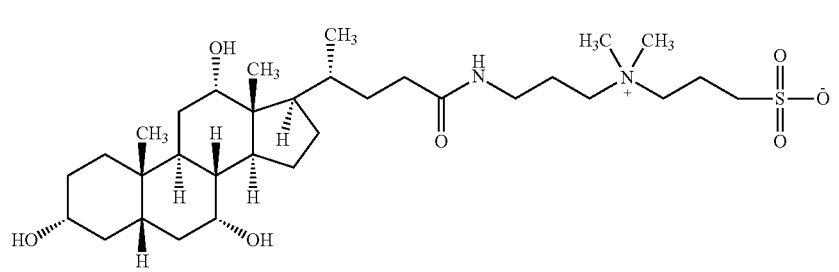
[Formula 2]

7. The method according to claim 1, wherein the mounting solution composition comprises 30 to 60 w/v % of the compound represented by formula 2, the optical isomer thereof, the hydrate thereof, or the salt thereof:

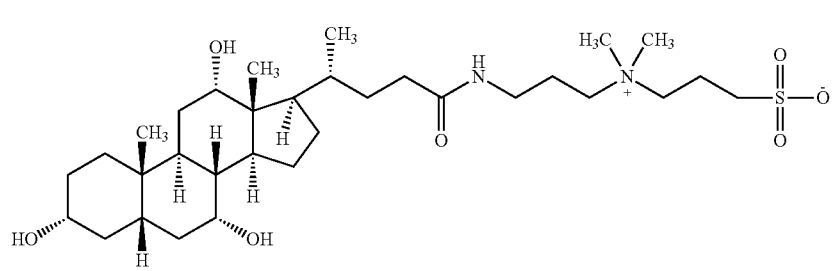
[Formula 2]

8. The method according to claim 1, wherein the mounting solution composition further comprises urea.

9. The method according to claim 1, wherein said contacting results in size reduction of the cleared biological tissue.

10. The method according to claim 1, wherein the alkali metal salt comprises sodium chloride.

11. A method of imaging a biological tissue using a microscope comprising:

a step of adjusting the size of a cleared biological tissue before microscopic observation by contacting the cleared biological tissue with a mounting solution composition comprising a compound represented by formula 2, an optical isomer thereof, a hydrate thereof, or a salt thereof, and an alkali metal salt, wherein the cleared biological tissue is a biological tissue treated with a clearing composition for tissue clearing; and a step of observing the biological tissue after the step of adjusting:

[Formula 2]
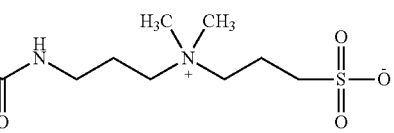
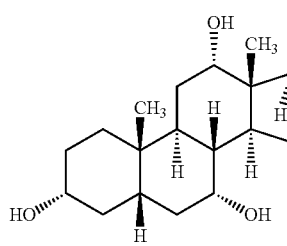
12. The method according to claim 11, further comprising a step of clearing a biological tissue to produce the cleared biological tissue.

UNITED STATES PATENT AND TRADEMARK OFFICE
CERTIFICATE OF CORRECTION

Page 1 of 1

PATENT NO. : 11,168,108 B2
APPLICATION NO. : 16/473365
DATED : November 9, 2021
INVENTOR(S) : Ki-Suk Kim, Sun Hyun Park and Dae-hwan Nam It is certified that error appears in the above-identified patent and that said Letters Patent is hereby corrected as shown below:

In the Claims

In Column 9, Claim 1, Lines 1-13, please delete:

"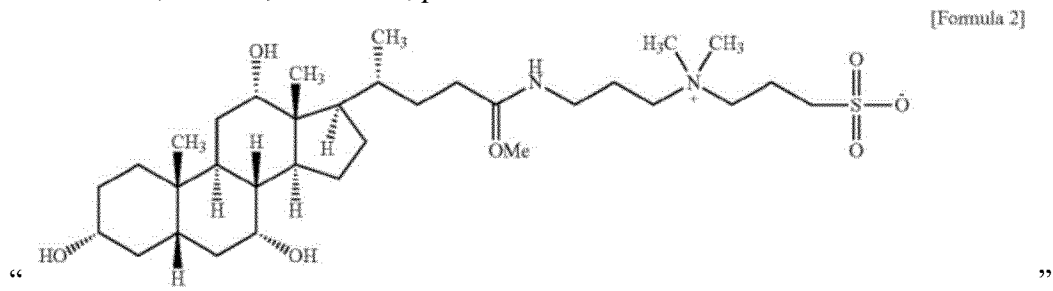"

And insert:

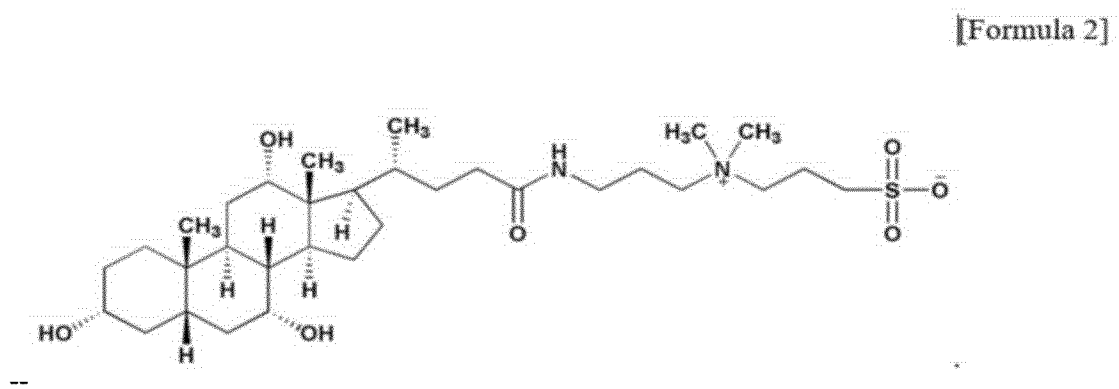

--                                                                                              --

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*